US006362389B1

(12) United States Patent
McDowall et al.

(10) Patent No.: US 6,362,389 B1
(45) Date of Patent: Mar. 26, 2002

(54) ELASTIC ABSORBENT STRUCTURES

(75) Inventors: Debra Jean McDowall, Roswell; Charles Allen Smith, Snellville; Melanie Stephens Winstanley, Alpharetta, all of GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/197,268

(22) Filed: Nov. 20, 1998

(51) Int. Cl.[7] ............................................. A61F 13/15
(52) U.S. Cl. ....................... 604/367; 604/364; 604/368; 604/373; 604/385.16
(58) Field of Search ...................... 604/364, 367, 604/368, 373, 385.16; 442/328, 329, 333, 382, 385, 400–401

(56) References Cited

U.S. PATENT DOCUMENTS

| 3,338,992 A | | 8/1967 | Kinney ........................ 264/24 |
| 3,341,394 A | | 9/1967 | Kinney ........................ 161/72 |
| 3,485,706 A | | 12/1969 | Evans ........................ 161/72 |
| 3,502,538 A | | 3/1970 | Petersen ...................... 161/150 |
| 3,502,763 A | | 3/1970 | Hartmann .................... 264/210 |
| 3,542,615 A | | 11/1970 | Dobo et al. ................. 156/181 |
| 3,692,618 A | | 9/1972 | Dorschner et al. ........... 161/72 |
| 3,802,817 A | | 4/1974 | Matsuki et al. ............... 425/66 |
| 3,849,241 A | | 11/1974 | Butin et al. ................. 161/169 |
| 3,855,046 A | | 12/1974 | Hansen et al. .............. 161/150 |
| 3,901,236 A | | 8/1975 | Assarsson et al. ........... 128/284 |
| 3,966,865 A | | 6/1976 | Nishida et al. .............. 264/147 |
| 4,076,663 A | | 2/1978 | Masuda et al. ........ 260/17.4 GC |
| 4,100,324 A | | 7/1978 | Anderson et al. ........... 428/288 |
| 4,286,082 A | | 8/1981 | Tsubakimoto et al. ...... 526/240 |
| 4,340,563 A | | 7/1982 | Appel et al. ................. 264/518 |
| 4,369,156 A | | 1/1983 | Mathes et al. .............. 264/147 |
| 4,530,353 A | | 7/1985 | Lauritzen .................... 128/156 |
| 4,542,199 A | | 9/1985 | Kaminsky et al. .......... 526/160 |
| 4,547,420 A | | 10/1985 | Krueger et al. ............. 428/229 |
| 4,588,630 A | | 5/1986 | Shimalla ..................... 428/131 |
| 4,729,371 A | | 3/1988 | Krueger et al. ........ 128/206.19 |
| 4,767,825 A | | 8/1988 | Pazos et al. ................. 525/408 |
| 4,795,668 A | | 1/1989 | Krueger et al. ............. 428/174 |
| 4,803,117 A | * | 2/1989 | Daponte ..................... 428/228 |
| 4,818,464 A | | 4/1989 | Lau ............................ 264/510 |
| 4,923,914 A | | 5/1990 | Nohr et al. .................. 524/99 |
| 5,057,166 A | | 10/1991 | Young, Sr. et al. ........ 156/62.2 |
| 5,064,689 A | | 11/1991 | Young, Sr. et al. ........ 427/202 |
| 5,064,802 A | | 11/1991 | Stevens et al. .............. 502/155 |
| 5,108,820 A | | 4/1992 | Kaneko et al. .............. 428/198 |
| 5,169,706 A | * | 12/1992 | Collier, IV et al. ......... 428/152 |
| 5,189,192 A | | 2/1993 | LaPointe et al. ............. 556/11 |
| 5,204,429 A | | 4/1993 | Kaminsky et al. .......... 526/308 |
| 5,225,014 A | | 7/1993 | Ogata et al. ................ 156/73.2 |
| 5,230,959 A | | 7/1993 | Young, Sr. et al. ......... 428/372 |
| 5,260,126 A | * | 11/1993 | Collier, IV et al. ......... 428/288 |
| 5,272,236 A | | 12/1993 | Lai et al. .................... 526/348.5 |
| 5,278,272 A | | 1/1994 | Lai et al. .................... 526/348.5 |
| 5,288,791 A | * | 2/1994 | Collier, IV et al. ......... 524/505 |
| 5,290,626 A | | 3/1994 | Nishio et al. ............... 428/224 |
| 5,302,447 A | | 4/1994 | Ogata et al. ................. 428/288 |
| 5,308,906 A | * | 5/1994 | Tayler et al. ................ 524/398 |
| 5,332,613 A | * | 7/1994 | Tayler et al. ................ 428/152 |
| 5,336,552 A | | 8/1994 | Strack et al. ................ 428/224 |
| 5,349,100 A | | 9/1994 | Mintz ......................... 585/350 |
| 5,352,749 A | | 10/1994 | DeChellis et al. ........... 526/68 |
| 5,372,885 A | | 12/1994 | Tabor et al. ................. 428/373 |
| 5,374,696 A | | 12/1994 | Rosen et al. ................. 526/126 |
| 5,382,400 A | | 1/1995 | Pikel et al. .................. 264/168 |
| 5,424,115 A | | 6/1995 | Stokes ........................ 428/198 |
| 5,432,000 A | | 7/1995 | Young, Sr. et al. ......... 428/372 |
| 5,511,960 A | | 4/1996 | Terakawa et al. ............ 425/7 |
| 5,516,585 A | | 5/1996 | Young, Sr. et al. ......... 428/372 |
| 5,645,542 A | | 7/1997 | Anjur et al. ................. 604/368 |
| 5,670,044 A | | 9/1997 | Ogata et al. ............. 210/497.01 |
| 5,676,660 A | * | 10/1997 | Mukaida et al. ............ 604/375 |
| 5,679,042 A | | 10/1997 | Varona ........................ 442/347 |
| 5,681,305 A | | 10/1997 | Korpman .................... 604/390 |
| 5,759,926 A | | 6/1998 | Pike et al. ................... 442/333 |
| 5,789,065 A | * | 8/1998 | Haffner et al. .............. 428/152 |
| 5,853,881 A | * | 12/1998 | Estey et al. ................. 428/373 |
| 5,964,743 A | * | 10/1999 | Abuto et al. ............... 604/385.1 |

FOREIGN PATENT DOCUMENTS

| EP | 315 507 | 5/1989 | ............ D04H/5/02 |
| EP | 333 209 | 9/1989 | ............ D04H/1/44 |
| EP | 341 870 | 11/1989 | ............ A61L/15/01 |
| EP | 492 554 | 7/1992 | ............ D04H/1/44 |
| EP | 534 863 | 3/1993 | ............ D04H/1/54 |
| JP | 04-065568 A | 3/1992 | ............ D04H/3/14 |
| JP | 07-138866 A | 5/1995 | ............ D04H/3/14 |
| WO | 98/03710 | 1/1998 | ............ D04H/3/14 |
| WO | 98/45519 | 10/1998 | ............ D04H/1/54 |

OTHER PUBLICATIONS

*Encyclopedia of Polymer Science and Engineering*, A Wiley–Interscience Publication, John Wiley & Sons, vol. 3, 299–300, 1985.

Wagener, K.B.: Oscillating Catalysts: A New Twist for Plastics, *Science*, vol. 267, 191, Jan. 13, 1995.

Coates, Geoffrey W. and Waymouth, Robert M.: Oscillating Stereocontrol: A Strategy for the Synthesis of Thermoplastic Elastomeric Polypropylene, *Science*, vol. 267, 217–219, Jan. 13, 1995.

J.M.G. Cowie: *Polymers: Chemistry and Physics of Modern Materials*, 142–145, International Textbook Co., Ltd., 1973.

* cited by examiner

*Primary Examiner*—John G. Weiss
*Assistant Examiner*—Michael Bogart
(74) *Attorney, Agent, or Firm*—Pauley Petersen Kinne & Erickson

(57) ABSTRACT

An absorbent elastic nonwoven material having improved conformability includes a matrix of thermoplastic elastomeric nonwoven filaments, present in an amount of about 3 to less than 20% by weight of the absorbent elastic nonwoven material. A plurality of absorbent fibers and a superabsorbent material are contained within the matrix, each constituting about 20–77% by weight of the absorbent elastic nonwoven material. The absorbent elastic nonwoven material is useful in a wide variety of personal care and medical absorbent articles where softness and conformability, as well as absorbency and elasticity, are important.

30 Claims, No Drawings

ELASTIC ABSORBENT STRUCTURES

FIELD OF THE INVENTION

This invention relates to nonwoven elastic absorbent materials having improved conformability at low levels of loading. More specifically, the invention relates to a combination of nonwoven elastomeric filaments, pulp fibers and a superabsorbent material, having greater flexibility and conformability than conventional elastomeric absorbent materials.

BACKGROUND OF THE INVENTION

Elastomeric absorbent materials have been evaluated in a variety of personal care structures including, without limitation, diapers, training pants, sanitary napkins, wipes, bibs, wound dressings, and surgical caps or drapes. U.S. Pat. No. 5,645,542 issued to Anjur et al., discloses an elastomeric absorbent structure made from a combination of thermoplastic elastomer fibers and wettable staple fibers. The reference discloses useful ranges of about 20–80% by weight staple fibers, and about 20–80% by weight elastomeric fibers, with intermediate amounts being preferred. Useful staple fibers include wood pulp fibers, modified cellulose fibers, textile fibers such as cotton or rayon, and substantially nonabsorbent synthetic polymer fibers.

The patent to Anjur et al. also discloses that a hydrogel-forming polymer can be added to increase the absorbency. The hydrogel-forming polymer may constitute about 15–60% by weight of the structure, with intermediate amounts being preferred.

Conventional elastic absorbent materials typically stretch under a fairly high tensile load, and tend to recover to an unstretched state when the load is relaxed or released. The relatively high retractive force associated with these structures is often unnecessary, and is sometimes undesirable. For instance, a high retractive force present in a personal care article may cause the article to have an uncomfortably tight fit. Also, a high retractive force may reduce the absorbency of an article by physically inhibiting the swelling of an absorbent material contained within the article.

For these reasons, there is a need or desire for an elastic nonwoven absorbent material which is more conformable and has less retractive force. There is also a need or desire for a less expensive elastic nonwoven absorbent material which requires lower amounts of the elastic filament ingredient, and relatively greater amounts of a less expensive absorbent material.

SUMMARY OF THE INVENTION

The present invention is directed to a conformable, comfortable, and highly absorbent elastic nonwoven material which addresses the foregoing concerns. The absorbent nonwoven material of the invention includes a mixture of nonwoven elastomeric polymer filaments, absorbent fibers, and superabsorbent particles or fibers. The elastomeric polymer filaments may be substantially continuous or staple in length, and preferably are substantially continuous. The nonwoven elastomeric polymer filaments constitute less than 20% by weight of the absorbent nonwoven material, and at least about 3% by weight of the absorbent nonwoven material. The absorbent fibers and superabsorbent particles or fibers each constitute about 20–77% by weight of the absorbent nonwoven material.

The absorbent nonwoven material of the invention can be stretched to at least about 110% of its original unstretched length, using a lower tensile load per basis weight than similar composite materials containing higher elastic filament levels. This low stretching force also means there is less retractive force when the absorbent nonwoven material is stretched. The low stretching force, and corresponding low retractive force, causes absorbent articles made from the material to have better comfort and better absorption. The improved absorption is attributed, in part, to the fact that there is less elastic restraint on the swelling of the superabsorbent polymer ingredient.

The absorbent nonwoven material of the invention is also relatively inexpensive to produce, because the lower amount of elastomeric polymer filaments permits inclusion of a correspondingly higher amount of the less expensive pulp fibers. Also, the absorbent nonwoven material of the invention exhibits better wicking than conventional elastomeric absorbent materials.

DEFINITIONS

The term "nonwoven fabric or web" means a web having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The term also includes films that have been perforated or otherwise treated to allow air to pass through. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.) The term "microfibers" means small diameter fibers having an average diameter not greater than about 75 microns, for example, having an average diameter of from about 1 micron to about 50 microns, or more particularly, having an average diameter of from about 1 micron to about 30 microns.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al. Spunbond fibers are quenched and generally not tacky on the surface when they enter the draw unit, or when they are deposited onto a collecting surface. Spunbond fibers are generally continuous and may have average diameters larger than 7 microns, often between about 10 and 30 microns.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface. Meltblown fibers used in the invention are preferably substantially continuous.

The term "polymer" generally includes but is not limited to, homopolymers, copolymers, including block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

The term "substantially continuous filaments or fibers" refers to filaments or fibers prepared by extrusion from a spinnerette, including without limitation spunbonded and meltblown fibers, which are not cut from their original length prior to being formed into a nonwoven web or fabric. Substantially continuous filaments or fibers may have lengths ranging from greater than about 15 cm to more than one meter; and up to the length of the nonwoven web or fabric being formed. The definition of "substantially continuous filaments or fibers" includes those which are not cut prior to being formed into a nonwoven web or fabric, but which are later cut when the nonwoven web or fabric is cut.

The term "staple filaments or fibers" means filaments or fibers which are natural or which are cut from a manufactured filament prior to forming into a web, and which have a length ranging from about 0.1–15 cm, more commonly about 0.2–7 cm.

The term "fiber" or "fibrous" is meant to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less.

The term "wettable" is meant to refer to a fiber which exhibits a liquid such as water, synthetic urine, or a 0.9 weight percent aqueous saline solution, in air contact angle of less than 90°. The contact angle may be determined, for example, in accordance with ASTM D724-89.

The term "thermoplastic" is meant to describe a material that softens when exposed to heat and which substantially returns to its original condition when cooled to room temperature.

The terms "elastic" and "elastomeric" are used interchangeably to mean a material that is generally capable of recovering its shape after deformation when the deforming force is removed. Specifically, as used herein, elastic or elastomeric is meant to be that property of any material which upon application of a biasing force, permits that material to be stretchable to a stretched biased length which is at least about 25 percent greater than its relaxed unbiased length, and that will cause the material to recover at least 40 percent of its elongation upon release of the stretching elongating force. A hypothetical example which would satisfy this definition of an elastomeric material would be a one (1) inch sample of a material which is elongatable to at least 1.25 inches and which, upon being elongated to 1.25 inches and released, will recover to a length of not more than 1.15 inches. Many elastic materials may be stretched by much more than 25 percent of their relaxed length, and many of these will recover to substantially their original relaxed length upon release of the stretching, elongating force. This latter class of materials is generally beneficial for purposes of the present invention.

The term "recover" or "retract" relates to a contraction of a stretched material upon termination of a biasing force following stretching of the material by application of the biasing force.

The term "superabsorbent material" refers to a water swellable, water-insoluble organic or inorganic material capable, under the most favorable conditions, of absorbing at least about 15 times its weight, preferably at least about 30 times its weight in an aqueous solution containing 0.9% by weight sodium chloride.

The term "pulp fibers" refers to fibers from natural sources such as woody and non-woody plants. Woody plants include, for example, deciduous and coniferous trees. Non-woody plants include, for instance, cotton, flax, esparto grass, milkweed, straw, jute hemp, and bagasse.

The term "average pulp fiber length" refers to a weighted average length of pulp determined using a Kajaani fiber analyzer Model No. FS-100 available from Kajaani Oy Electronics in Kajaani, Finland. Under the test procedure, a fiber sample is treated with a macerating liquid to ensure that no fiber bundles or shives are present. Each fiber sample is dispersed in hot water and diluted to about a 0.001% concentration. Individual test samples are drawn in approximately 50 to 500 ml portions from the dilute solution and tested using the standard Kajaani fiber analysis procedure. The weighted average fiber lengths may be expressed by the following equation:

$$\sum_{X_i>0}^{k} (X_i * n_i)/n$$

where
  k=maximum fiber length,
  $X_i$=individual fiber length,
  $n_i$=number of fibers having length $X_i$
and
  n=total number of fibers measured.

The term "bicomponent filaments or fibers" refers to fibers which have been formed from at least two polymers extruded from separate extruders but spun together to form one fiber. The polymers are arranged in substantially constantly positioned distinct zones across the cross section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement or an "islands-in-the-sea" arrangement. Bicomponent fibers are taught in U.S. Pat. No. 5,108,820 to Kaneko et al., U.S. Pat. No. 5,336,552 to Strack et al., and U.S. Pat. No. 5,382,400 to Pike et al., each of which is incorporated herein in its entirety by reference. For two component fibers, the polymers may be present in ratios of 75/25, 50/50, 25/75 or any other desired ratios. Conventional additives, such as pigments and surfactants, may be incorporated into one or both polymer streams, or applied to the filament surfaces.

The term "personal care absorbent article" includes diapers, training pants, swim wear, absorbent underpants, adult incontinence products, and feminine hygiene products.

The term "through-air bonding" or "TAB" means a process of bonding a nonwoven, for example, a bicomponent fiber web in which air which is sufficiently hot to melt one of the polymers of which the fibers of the web are made is forced through the web. The air velocity is often between 100 and 500 feet per minute and the dwell time may be as long as 6 seconds. The melting and resolidification of the polymer provides the bonding. Through-air bonding has restricted variability and is generally regarded as a second step bonding process. Since TAB requires the melting of at least one component to accomplish bonding, it is restricted to webs with two components such as bicomponent fiber webs or webs containing an adhesive fiber or powder.

The term "thermal point bonding" involves passing a fabric or web of fibers to be bonded between a heated calender roll and an anvil roll. The calender roll is usually, though not always, patterned in some way so that the entire fabric is not bonded across its entire surface. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen and Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds and a wire weave pattern looking as the name suggests, e.g., like a window screen. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

DETAILED DESCRIPTION OF THE PRESENTLY PREFERRED EMBODIMENTS

In accordance with the invention, an absorbent elastic nonwoven web composite having high loading of an absorbent material and excellent conformability is provided. The absorbent elastic nonwoven web composite includes about 3 to less than 20 percent by weight of an elastic filament matrix including a plurality of thermoplastic elastomeric nonwoven filaments, about 20–77% by weight absorbent fibers, and about 20–77% by weight of a superabsorbent material. The absorbent fibers and superabsorbent material are contained in the matrix. Preferably, the absorbent elastic nonwoven web composite includes about 5–18% by weight of the elastic filament matrix, about 25–70% by weight absorbent fibers, and about 25–70% by weight superabsorbent material. More preferably, the absorbent elastic nonwoven web composite includes about 5–15% by weight of the elastic filament matrix, about 30–62% by weight absorbent fibers, and about 40–65% by weight superabsorbent material.

Materials suitable for use in preparing the thermoplastic elastomeric fibers herein include diblock, triblock, or multiblock elastomeric copolymers such as olefinic copolymers, including styrene-isoprene-styrene, styrene-butadiene-styrene, styrene-ethylene/butylene-styrene, or styrene-ethylene/propylene-styrene, which may be obtained from the Shell Chemical Company, under the trade designation KRATON® elastomeric resin; polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; and single-site or metallocene-catalzed polyolefins having density less than about 0.89 grams/cc, available from Dow Chemical Co. under the trade name AFFINITY®.

A number of block copolymers can be used to prepare the thermoplastic elastomeric fibers useful in this invention. Such block copolymers generally comprise an elastomeric midblock portion and a thermoplastic endblock portion. The block copolymers used in this invention generally have a three-dimensional physical crosslinked structure below the endblock portion glass transition temperature ($T_2$) and are elastomeric. The block copolymers are also thermoplastic in the sense that they can be melted, formed, and resolidified several times with little or no change in physical properties (assuming a minimum of oxidative degradation).

One way of synthesizing such block copolymers is to polymerize the thermoplastic endblock portions separately from the elastomeric midblock portions. Once the midblock and endblock portions have been separately formed, they can be linked. Typically, midblock portions can be obtained by polymerizing di- and tri-unsaturated $C_4$–$C_{10}$ hydrocarbons such as, for example, dienes such as butadiene, isoprene, and the like, and trienes such as 1, 3, 5-heptatriene, and the like. When an endblock portion A is joined to a midblock portion B, an A—B block copolymer unit is formed, which unit can be coupled by various techniques or with various coupling agents C to provide a structure such as A—B—A, which is believed to comprise two A—B blocks joined together in a tail-to-tail A—B—C—B—A arrangement. By a similar technique, a radial block copolymer can be formed having the formula $(A—B)_nC$, wherein C is the hub or central polyfunctional coupling agent and n is a number greater than 2. Using the coupling agent technique, the functionality of C determines the number of A—B branches.

Endblock portion A generally comprises a poly (vinylarene), such as polystyrene, having an average molecular weight between 1,000 and 60,000. Midblock portion B generally comprises a substantially amorphous polyolefin such as polyisoprene, ethylene/propylene polymers, ethylene/butylene polymers, polybutadiene, and the like, or mixtures thereof, having an average molecular weight between about 5,000 and about 450,000. The total molecular weight of the block copolymer is suitably about 10,000 to about 500,000 and more suitably about 200,000 to about 300,000. Any residual unsaturation in the midblock portion of the block copolymer can be hydrogenated selectively so that the content of olefinic double bonds in the block copolymers can be reduced to a residual proportion of less than 5 percent and suitably less than about 2 percent. Such hydrogenation tends to reduce sensitivity to oxidative degradation and may have beneficial effects upon elastomeric properties.

Suitable block copolymers used in this invention comprise at least two substantially polystyrene endblock portions and at least one substantially ethylene/butylene midblock portion. As an example, ethylene/butylene typically may comprise the major amount of the repeating units in such a block copolymer and can constitute, for example, 70 percent by weight or more of the block copolymer. The block copolymer can have three or more arms, and good results can be obtained with, for example, four, five, or six arms. The midblock portion can be hydrogenated, if desired.

Linear block copolymers, such as A—B—A, A—B—A—B—A or the like, are suitably selected on the basis of endblock content, large endblocks being preferred. For polystyrene-ethylene/butylene-polystyrene block copolymers, a styrene content in excess of about 10 weight percent is suitable, such as between about 12 to about 30 weight percent. With higher styrene content, the polystyrene endblock portions generally have a relatively high molecular weight. A commercially available example of such a linear block copolymer is a styrene-ethylene/butylene-styrene block copolymer which contains about 13 weight percent styrene units and essentially the balance being ethylene/butylene units, commercially available from the Shell Chemical Company, under the trade designation KRATON® G1657 elastomeric resin. Typical properties of KRATON® G1657 elastomeric resin are reported to include a tensile strength of 3400 pounds per square inch ($2 \times 10^6$ kilograms per square meter), a 300 percent modulus of 350 pounds per square inch ($1.4 \times 10^5$ kilograms per square meter), an elongation of 750 percent at break, a Shore A hardness of 65, and a Brookfield viscosity, when at a concentration of 25 weight percent in a toluene solution, of about 4200 centipoise at room temperature. Another suitable elastomer, KRATON® G2740, is a styrene butadiene block copolymer blended with tackifier and low density polyethylene.

Other suitable elastomeric polymers may also be used to make the thermoplastic elastic fibers. These include, without limitation, elastomeric (single-site or metallocene catalyzed) polypropylene, polyethylene and other alpha-olefin homopolymers and copolymers, having density less than about 0.89 grams/cc; ethylene vinyl acetate copolymers; and substantially amorphous copolymers and terpolymers of ethylene-propylene, butene-propylene, and ethylene-propylene-butene.

Metallocene-catalyzed elastomeric polymers are relatively new, and are presently preferred. The metallocene process for making polyolefins uses a metallocene catalyst which is activated (i.e., ionized) by a co-catalyst.

Polymers produced using metallocene catalysts have a narrow molecular weight distribution. "Narrow molecular weight distribution polymer" refers to a polymer that exhibits a molecular weight distribution of less than about 3.5. As is known in the art, the molecular weight distribution of a polymer is the ratio of the weight average molecular weight of the polymer to the number average molecular weight of the polymer. Methods of determining molecular weight distribution are described in the *Encyclopedia of Polymer Science and Engineering*, Volume 3, Pages 299–300 (1985). Examples of narrow molecular weight distribution polyolefins include the metallocene-catalyzed polyolefins, the single-site catalyzed polyolefins, and the constrained geometry-catalyzed polyolefins described above. As is known in the art, the metallocene-catalyzed polyolefins and the constrained geometry-catalyzed polyolefins are sometimes referred to as types of single-site catalyzed polymers. Polydispersities ($M_w/M_n$) of below 3.5 and as even below 2 are possible for metallocene produced polymers. These polymers also have a narrow short chain branching distribution when compared to otherwise similar Ziegler-Natta produced polymers.

Metallocene catalysts include bis(n-butylcyclopentadienyl) titanium dichloride, bis(n-butylcyclopentadienyl)zirconium dichloride, bis(cyclopentadienyl)scandium chloride, bis(indenyl) zirconium dichloride, bis(methylcyclopentadienyl)titanium dichloride, bis(methylcyclopentadienyl)zirconium dichloride, cobaltocene, cyclopentadienyltitanium trichloride, ferrocene, haflocene dichloride, isopropyl (cyclopentadienyl$_1$-1-flourenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow.

The metallocene process, and particularly the catalysts and catalyst support systems are the subject of a number of patents. U.S. Pat. No. 4,542,199 to Kaminsky et al. describes a procedure wherein a metallocene catalyst of the general formula (cyclopentadienyl)2MeRHal wherein Me is a transition metal, Hal is a halogen and R is cyclopentadienyl or a C1 to C6 alkyl radical or a halogen, is used to form polyethylene. U.S. Pat. No. 5,189,192 to LaPointe et al. and assigned to Dow Chemical describes a process for preparing addition polymerization catalysts via metal center oxidation. U.S. Pat. No. 5,352,749 to Exxon Chemical Patents, Inc. describes a method for polymerizing monomers in fluidized beds. U.S. Pat. No. 5,349,100 describes chiral metallocene compounds and preparation thereof by creation of a chiral center by enantioselective hydride transfer.

Co-catalysts are materials such as methylaluminoxane (MAO) which is the most common, other alkylaluminums and boron containing compounds like tris (pentafluorophenyl)boron, lithium tetrakis (pentafluorophenyl)boron, and dimethylanilinium tetrakis (pentafluorophenyl)boron. Research is continuing on other co-catalyst systems or the possibility of minimizing or even eliminating the alkylaluminums because of handling and product contamination issues. The important pont is that the metallocene catalyst be activated or ionized to a cationic form for reaction with the monomer(s) to be polymerized.

It is also possible using a metallocene catalyst system to control the isotacticity of the polymer quite closely when stereo selective metallocene catalysts are employed. In fact, polymers have been produced having an isotacticity in excess of 99 percent. It is also possible to produce highly syndiotactic polypropylene using this system.

Controlling the isotacticity of a polymer can also result in the production of a polymer which contains blocks of isotactic and blocks of atactic material alternating over the length of the polymer chain. This construction results in an elastic polymer by virtue of the atactic portion. Such polymer synthesis is discussed in the journal *Science*, Volume 267 (Jan. 13, 1995) at Page 191 in an article by K. B. Wagner. Wagner, in discussing the work of Coates and Waymouth, explains that the catalyst oscillates between the stereochemical forms resulting in a polymer chain having running lengths of isotactic stereocenters connected to running lengths of atactic centers. Isotactic dominance is reduced producing elasticity. Geoffrey W. Coates and Robert M. Waymouth, in an article entitled "Oscillating Stereocontrol: A Strategy for the Synthesis of Thermoplastic Elastomeric Polypropylene" at Page 217 in the same issue, discuss their work in which they used metallocene bis(2-phenylindenyl)-zirconium dichloride in the presence of methylaluminoxane (MAO), and, by varying the pressure and temperature in the reactor, oscillate the polymer form between isotactic and atactic.

Commercial production of metallocene polymers is somewhat limited but growing. Such polymers are available from Exxon Chemical Company of Baytown, Tex. under the trade name EXXPOL® for polypropylene based polymers and EXACT® for polyethylene based polymers. Dow chemical company of Midland, Mich. has polymers commercially available under the name ENGAGE®. These materials are believed to be produced using non-stereo selective metallocene catalysts. Exxon generally refers to their metallocene catalyst technology as "single site" catalysts while Dow refers to theirs as "constrained geometry" catalysts under the name INSIGHT® to distinguish them from traditional Ziegler-Natta catalysts which have multiple reaction sites. Other manufacturers such as Fina Oil, BASF, Amoco, Hoechst and Mobil are active in this area and it is believed that the availability of polymers produced according to this technology will grow substantially in the next decade.

Regarding metallocene based elastomeric polymers, U.S. Pat. No. 5,204,429 to Kaminsky et al. describes a process which may produce elastic copolymers from cycloolefins and linear olefins using a catalyst which is a stereorigid chiral metallocene transition metal compound and an aluminoxane. The polymerization is carried out in an inert solvent such as an aliphatic or cycloaliphatic hydrocarbon such as toluene. The reaction may also occur in the gas phase using the monomers to be polymerized as the solvent. U.S. Pat. No. 5,278,272 and 5,272,236, both to Lai et al., assigned to Dow Chemical and entitled "Elastic Substantially Linear Olefin Polymers" describe polymers having particular elastic properties. Dow also commercially produces a line of elastomeric polyolefins under the trade name ENGAGE®.

The elastomeric fibers may be substantially continuous or staple in length, but are preferably substantially continuous. Substantially continuous filaments exhibit better containment of the cellulose fibers and superabsorbent material, have better elastic recovery and provide better distribution of liquids, than staple length fibers. The elastomeric fibers may be produced using a spunbonding process, a meltblowing process, or another suitable process. The elastomeric fibers may have an average diameter of about 1–75 microns, preferably about 1–40 microns, more preferably about 1–30 microns.

The thermoplastic elastomeric fibers may be circular but may also have other cross-sectional geometries such as elliptical, rectangular, triangular or multilobal. The thermoplastic elastomeric fibers may be wettable. The thermoplastic elastomeric fibers may be made wettable by first preparing the thermoplastic elastomeric fibers and then subsequently applying a hydrophilizing surface treatment to the fibers.

Alternatively, the thermoplastic elastomeric fibers may be made wettable by adding a hydrophilic ingredient to the polymer prior to spinning. In general, any polymeric component capable of being polymerized with the thernoplastic elastomeric component, capable of hydrophilizing the resultant copolymeric material to render it wettable, wherein the hydrophilizing component does not substantially affect the elastic properties of the prepared fiber, is suitable for use in the present invention. Hydrophilic ingredients suitable for use in the present invention include without limitation polyethylene oxide and polyvinyl alcohol, as well as a wide variety of commercial hydrophilic surfactants.

In still another embodiment, the thermoplastic elastomeric fibers may be bicomponent or biconstituent filaments, in which one of the polymer components is hydrophilic or rendered hydrophilic. An exemplary embodiment is a sheath/core bicomponent filament having a hydrophilic core surrounded by a hydrophilic sheath. Internal and/or topical treatments can be applied to one or both polymer components of the bicomponent filaments. Other additives such as pigments can also be included in the elastomeric filaments.

The absorbent fibers may be any liquid-absorbing natural or synthetic fibers which are capable, under the most favorable conditions, of absorbing about 1 to less than 15 times their weight in an aqueous solution containing 0.9% by weight sodium chloride. Absorbent fibers include without limitation rayon staple fibers, cotton fibers, natural cellulose fibers such as wood pulp fibers and cotton linters, other pulp fibers, and fiberized feathers (e.g., fiberized poultry feathers, such as fiberized chicken feathers.)

Pulp fibers are especially useful as the absorbent fibers in the elastomeric nonwoven web composite. Preferred pulp fibers include cellulose pulp fibers. The pulp fibers may be any high average fiber length pulp, low average fiber length pulp, or mixtures of them.

The term "high average fiber length pulp" refers to pulp that contains a relatively small amount of short fibers and non-fiber particles. High fiber length pulps typically have an average fiber length greater than about 1.5 mm, preferably about 1.5–6 mm, as determined by an optical fiber analyzer, such as the Kajaani tester referenced above. Sources generally include non-secondary (virgin) fibers as well as secondary fiber pulp which has been screened. Examples of high average fiber length pulps include bleached and unbleached virgin softwood fiber pulps.

The term "low average fiber length pulp" refers to pulp that contains a significant amount of short fibers and non-fiber particles. Low average fiber length pulps have an average fiber length less than about 1.5 mm, preferably about 0.7–1.2 mm, as determined by an optical fiber analyzer such as the Kajaani tester referenced above. Examples of low fiber length pulps include virgin hardwood pulp, as well as secondary fiber pulp from sources such as office waste, newsprint, and paperboard scrap.

Examples of high average fiber length wood pulps include those available from the U.S. Alliance Coosa Pines Corporation under the trade designations Longlac 19, Coosa River 56, and Coosa River 57. The low average fiber length pulps may include certain virgin hardwood pulp and secondary (i.e., recycled) fiber pulp from sources including newsprint, reclaimed paperboard, and office waste. Mixtures of high average fiber length and low average fiber length pulps may contain a predominance of low average fiber length pulps.

The pulp fibers may be unrefined or may be beaten to various degrees of refinement. Crosslinking agents and/or hydrating agents may also be added to the pulp mixture. Debonding agents may be added to reduce the degree of hydrogen bonding if a very open or loose nonwoven pulp fiber web is desired. One exemplary debonding agent is available from the Quaker Oats Chemical Company, Conshohocken, Pa., under the trade designation Quaker 2008. The addition of certain debonding agents in the amount of, for example, 1–4% by weight of the composite, may reduce the measured static and dynamic coefficients of friction and improve the abrasion resistance of the thermoplastic continuous polymer filaments. The debonding agents act as lubricants or friction reducers. Debonded pulp fibers are commercially available from Weyerhaeuser Corp. under the designation NB405.

The superabsorbent material may be in the form of fibers, particles, or combinations thereof. As explained above, the term "superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride.

The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic superabsorbent material polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further superabsorbent materials include natural and modified natural polymers, such as hydrolyzed acrylonitrilegrafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic super-absorbent polymers can also be useful in the present invention. Other suitable absorbent gelling materials are disclosed by Assarsson et al. in U.S. Pat. No. 3,901,236 issued August 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbent materials may be xerogels which form hydrogels when wetted. The term "hydrogel," however, has commonly been used to also refer to both the wetted and unwetted forms of the superabsorbent polymer material. The superabsorbent materials can be in many forms such as flakes, powders, particulates, fibers, continuous fibers, networks, solution spun filaments and webs. The particles can be of any desired shape, for example, spiral or semi-spiral, cubic, rod-like, polyhedral, etc. Needles, flakes, fibers, and combinations may also be used.

Superabsorbents are generally available in particle sizes ranging from about 20 to about 1000 microns. Examples of suitable commercially available particulate superabsorbents include SANWET® IM 3900 and SANWET® IM-5000P, available from Hoescht Celanese located in Portsmouth, Va., DRYTECH® 2035LD available from Dow Chemical Co. located in Midland, Mich., and FAVOR® SXM 880, available from Stockhausen located in Greensborough, N.C. An example of a fibrous superabsorbent is OASIS® 101, available from Technical Absorbents, located in Grimsby, United Kingdom.

The thermoplastic elastomeric nonwoven filaments may be combined with the absorbent and superabsorbent materials using processes well known in the art. For example, a coform process may be employed, in which at least one meltblown diehead is arranged near a chute through which other materials are added while the web is forming. Coform processes are described in U.S. Pat. Nos. 4,818,464 to Lau and 4,100,324 to Anderson et al., the disclosures of which are incorporated by reference. The thermoplastic elastomeric filaments and absorbent and superabsorbent material may also be combined using hydraulic entangling or mechanical entangling. A hydraulic entangling process is described in U.S. Pat. No. 3,485,706 to Evans, the disclosure of which is incorporated by reference. After combining the ingredients, the absorbent elastic nonwoven composite may be bonded together using the through-air bonding or thermal point bonding techniques described above, to provide a coherent high integrity structure.

Alternatively, the absorbent structures can be formed as layered structures using two die tips to extrude the elastomeric filaments, and injecting the absorbent and superabsorbent materials as a middle layer between two elastomeric filament layers. Various degrees of mixing of elastomeric filaments and the absorbent/superabsorbent materials can be accomplished to facilitate regions of greater and lesser concentration of elastomeric filaments. This layered structure is an alternative to the absorbent structures produced by a coform process, in which the absorbent ingredients are substantially evenly distributed among individual filaments of an elastomeric nonwoven web.

The absorbent elastic nonwoven material of the invention can be stretched to at least about 110% of its original unstretched length, using a ratio of tensile load to basis weight below that of similar materials containing 20% or more elastic filaments. Preferably, the ratio of tensile load to basis weight will be at least about 10% lower, more preferably at least about 25% lower, for absorbent elastic nonwoven materials of the invention, compared to those having 20% or more elastic filaments. The absorbent elastic nonwoven material is useful in personal care and medical absorbent applications where conformability, comfort, softness, high absorbency and relatively low cost may be important. Personal care absorbent articles include diapers, training pants, swim wear, absorbent underpants, baby wipes, adult incontinence products, feminine hygiene products, and the like. The absorbent elastic nonwoven material is especially useful in diapers, where softness conformability and high absorbency are all important. Other absorbent articles which may utilize the absorbent elastic nonwoven material include without limitation absorbent medical products, including underpads, elastic bandages, absorbent drapes, and medical wipes which contain alcohol and/or other disinfectants.

EXAMPLES

Sixteen absorbent elastic nonwoven composite materials were prepared using combinations of the following ingredients:

1. Weyerhaeuser NB405, a soft wood pulp obtained from Southern Pine trees, with a debonder.
2. U.S. Alliance Coosa Pines 1654, a soft wood pulp obtained from Southern Pine trees, with 16% hardwood.
3. Sappi Saiccor Eucalyptus, a low average fiber length pulp containing fine fibers, available from National-Gottesman, Inc., located in Purchase, N.Y.
4. KRATON® G2740, a commercial elastomer available from Shell Chemical Co., including a mixture of styrene-butadiene block copolymer with a tackifier and low density polyethylene. This elastomer was formed into meltblown filaments substantially continuous in length.
5. FAVOR® SXM 880, a particulate acrylate-based superabsorbent material available from Stockhausen Co.

The KRATON® filaments were spray treated with 0.4–2% of a surfactant system containing a 3:1 ratio (by active weight) of AHCOVEL® base N62 from Hodgson Textile & Chemical Co. and GLUCOPON® 220UP, available from Henkel Corporation. Then the filaments and absorbent ingredients were combined using a coform process similar to the one described in U.S. Pat. No. 4,100,324, issued to Anderson et al. The superabsorbent particles were added together with the pulp fibers into the stream of substantially continuous filaments being formed. For each type of pulp, different quantities of pulp and superabsorbent were incorporated into the elastomeric filaments, which were present at levels from 5% to at least 20% by weight, and up to about 40% by weight of the absorbent elastic nonwoven composite material.

The samples thus prepared were then tested using the following techniques:

Tensile Testing

The tensile tests were performed according to the INDA Strip Tensile test procedure IST 110.1-92. The sample was 3" wide instead of the 2" width described in IST 110.1-92. The test parameters included a) cross-head speed: 20"/min., b) load cell of 10 or 25 lbs., c) gage length of 3", and d) constant rate of extension.

The ultimate breaking load and elongation were determined from the breaking point which is defined as the point where the tensile load decreases by 75%, as determined by the instantaneous change in load at incremental changes in elongation.

Peak load is defined as the maximum load during the test, peak elongation is the elongation at that load.

Initial modulus was calculated as the stress/strain in the initial portion of the stress strain curve, where stress is calculated as the load/cross-sectional area and strain is the elongation divided by the initial length.

Cyclic Tensile Testing

For the cyclic tensile testing, the samples were prepared and conditioned according to the INDA Strip Tensile test procedure IST 110.1-92. The sample was 3" wide instead of the 2" width described in IST 110.1-92. The sample was mounted according to IST 110.1-92 in the clamp of the testing machine, which is the constant-rate-of-extension testing machine described in IST 110.1-92. The parameters of the cyclic testing are as follows:

Crosshead speed: 20 inches/minute

Load Cell: 10 or 25 pounds

Gage length: 3 inches

Number of cycles: 5

Extension per cycle: 100%

For each of the five cycles, the sample was extended to 100% of its original length (or 6 inches total) and returned to its original position (0% elongation or 3 inches). The properties recorded were % Hysteresis (% Energy Lost) for all cycles and % Set after the fifth cycle.

% Hysteresis (% Energy Lost) is the amount of energy lost within a specific cycle. This is calculated as the area between the loading and unloading curve for a specific cycle.

% Set is a measure of the remaining strain after removal of the applied stress. Set is calculated as the (Final length-initial length)/Initial length *100. The final length is determined on the unloading of the firth cycle, as the point where the load first reaches zero.

Saturated Capacity Testing

The saturated capacity, for each sample, was tested by soaking a 6"×9" sample of each composite material for 20 minutes in a 0.9% saline solution. Then, the sample was desorbed on a vacuum box at 0.5 psi for 5 minutes. The capacity was calculated as weight of wet sample minus weight of dry sample, the difference being divided by the dry sample weight. The results were recorded.

Compression

Some of the samples were compressed before testing using a heated hydraulic press at 110° F. with 1.3 mm shims, and a pressure of 20,000 lbs. for 10–50 seconds.

Table 1 (below) shows the test results for the sixteen absorbent elastic nonwoven composite materials. As seen from the Examples, for a given type of pulp, the ratio of Peak Load/Basis Weight usually increases with the percentage of elastic nonwoven filaments. This ratio is lower at elastic filament levels below 20%, than at elastic filament levels of 20% or greater. These differences, however, are more pronounced for the uncompressed samples than for the compressed samples. Similar trends are observed in the ratios of Load/Basis Weight at 10% elongation.

TABLE 1

| Example # | Pulp Type | % KRATON G 2740 | % Pulp | % FAVOR SXM 880 | Basis Weight gsm | Density g/cc | Saturated Capacity g/g | Peak Load/ Basis Wt. g/gsm |
|---|---|---|---|---|---|---|---|---|
| | Compressed | | | | | | | |
| 1 | NB-405 | 10 | 56 | 34 | 409 | 0.2 | 16.0 | 1.16 |
| 2 | NB-405 | 15 | 54 | 31 | 461 | 0.2 | 15.5 | 1.56 |
| 3 | NB-405 | 10 | 53 | 37 | 383 | 0.2 | 18.0 | 1.29 |
| 4 | NB-405 | 20 | 43 | 37 | 420 | 0.2 | 16.0 | 1.33 |
| 5 | Eucalyptus | 10 | 53 | 37 | 362 | 0.2 | 17.7 | 1.45 |
| 6 | Eucalyptus | 20 | 43 | 37 | 392 | 0.2 | 16.4 | 2.70 |
| 7 | Eucalyptus | 15 | 53 | 31 | 434 | 0.2 | 14.6 | 2.25 |
| 8 | Eucalyptus | 30 | 44 | 26 | 635 | 0.2 | 13.3 | 3.00 |
| 9 | 1654 | 15 | 54 | 31 | 451 | 0.2 | 12.8 | 2.00 |
| 10 | 1654 | 31 | 45 | 25 | 523 | 0.2 | 10.4 | 3.25 |
| 11 | 1654 | 41 | 38 | 21 | 370 | 0.2 | 10.2 | 2.65 |
| | Uncompressed | | | | | | | |
| 12 | NB-405 | 5 | 59 | 35 | 194 | .10 | 19.5 | 0.50 |
| 13 | NB-405 | 10 | 53 | 37 | 197 | .10 | 17.0 | 1.10 |
| 14 | NB-405 | 15 | 47 | 38 | 205 | .12 | 17.0 | 1.75 |
| 15 | NB-405 | 20 | 43 | 37 | 205 | .15 | 18.1 | 2.25 |

TABLE 1-continued

| | | | | | | | | |
|---|---|---|---|---|---|---|---|---|
| 16 | NB-405 | 5 | 57 | 38 | 403 | .11 | 19.5 | 0.50 |
| 17 | NB-405 | 10 | 55 | 35 | 392 | .11 | 17.5 | 0.93 |
| 18 | NB-405 | 15 | 49 | 36 | 395 | .12 | 16.2 | 3.00 |
| 19 | NB-405 | 20 | 43 | 37 | 396 | .16 | 15.5 | 2.41 |
| 20 | 1654 | 15 | 54 | 31 | 451 | .08 | 13.0 | 1.79 |
| 21 | 1654 | 31 | 45 | 25 | 523 | .10 | 11.4 | 6.49 |
| 22 | 1654 | 41 | 38 | 21 | 370 | .11 | 11.2 | 12.73 |
| 23 | Eucalyptus | 15 | 53 | 31 | 434 | .12 | 15.0 | 0.51 |
| 24 | Eucalyptus | 30 | 44 | 26 | 635 | .14 | 13.0 | 0.87 |

| Example # | Pulp Type | Elongation at Peak Load % | Ultimate Elongation % | Initial Modulus N/cm² | Load/BW at 10% Elongation g/gsm | 5 Cycle Testing at 100% Elongation | | |
|---|---|---|---|---|---|---|---|---|
| | | | | | | Cycle 1 % Energy Lost | Cycle 3 % Energy Lost | Cycle 5 % Set |
| | Compressed | | | | | | | |
| 1 | NB-405 | 12 | 152 | 19 | 1.13 | 87 | 43 | 25 |
| 2 | NB-405 | 20 | 197 | 27 | 1.25 | 80 | 38 | 20 |
| 3 | NB-405 | 16 | 125 | 21 | 1.15 | 84 | 40 | 23 |
| 4 | NB-405 | 25 | 228 | 24 | 1.02 | 75 | 37 | 18 |
| 5 | Eucalyptus | 235 | 384 | 13 | 0.63 | 75 | 41 | 25 |
| 6 | Eucalyptus | 250 | 459 | 32 | 1.39 | 65 | 27 | 12 |
| 7 | Eucalyptus | 40 | 252 | 33 | 1.25 | 73 | 31 | 16 |
| 8 | Eucalyptus | 35 | 299 | 99 | 1.87 | 70 | 31 | 17 |
| 9 | 1654 | 26 | 329 | 40 | 1.29 | 66 | 31 | 16 |
| 10 | 1654 | 415 | 433 | 36 | 1.90 | 66 | 31 | 14 |
| 11 | 1654 | 225 | 189 | 37 | 1.54 | 79 | 34 | 18 |
| | Uncompressed | | | | | | | |
| 12 | NB-405 | 28 | 125 | 2 | 0.19 | 76 | 28 | 24 |
| 13 | NB-405 | 150 | 150 | 7 | 0.55 | 73 | 32 | 28 |
| 14 | NB-405 | 239 | 250 | 10 | 0.70 | 73 | 33 | 29 |
| 15 | NB-405 | 266 | 275 | 14 | 0.76 | 65 | 29 | 26 |
| 16 | NB-405 | 27 | 100 | 4 | 0.26 | 81 | 34 | 28 |
| 17 | NB-405 | 34 | 125 | 5 | 0.40 | 73 | 33 | 29 |
| 18 | NB-405 | 266 | 266 | 10 | 0.65 | 80 | 38 | 35 |
| 19 | NB-405 | 242 | 242 | 17 | 0.97 | 68 | 32 | 30 |
| 20 | 1654 | 280 | 438 | 9 | 0.66 | 71 | 32 | 30 |
| 21 | 1654 | 440 | 590 | 18 | 1.15 | 61 | 27 | 12 |
| 22 | 1654 | 440 | 492 | 37 | 1.66 | 59 | 27 | 11 |
| 23 | Eucalyptus | 30 | 419 | 22 | 0.35 | 70 | 29 | 14 |
| 24 | Eucalyptus | 80 | 445 | 20 | 0.44 | 72 | 31 | 14 |

While the embodiments of the invention described herein are presently preferred, various modifications and improvements can be made without departing from the spirit and scope of the invention. The scope of the invention is indicated in the appended claims, and all changes that fall within the meaning and range of equivalents are intended to be embraced therein.

We claim:

1. An absorbent elastic nonwoven material comprising, by weight of the absorbent elastic nonwoven material:
    about 3 to 18% of an elastic filament matrix including a plurality of thermoplastic elastomeric nonwoven filaments; and
    contained within the matrix, about 20–77% of absorbent fibers and about 20–77% of a superabsorbent material.

2. The absorbent elastic nonwoven material of claim 1, comprising, by weight of the absorbent elastic nonwoven material, about 5–18% by weight of the elastic filament matrix, about 25–70% by weight of the absorbent fibers, and about 25–70% by weight of the superabsorbent material.

3. The absorbent elastic nonwoven material of claim 1, comprising, by weight of the absorbent elastic nonwoven material, about 5–15% of the elastic filament matrix, about 30–62% of the absorbent fibers, and about 40–65% of the superabsorbent material.

4. The absorbent elastic nonwoven material of claim 1, wherein the absorbent fibers and superabsorbent material are substantially evenly distributed among the elastic filaments.

5. The absorbent elastic nonwoven material of claim 1, wherein the thermoplastic elastomeric filaments comprise substantially continuous filaments.

6. The absorbent elastic nonwoven material of claim 1, wherein the thermoplastic elastomeric filaments comprise meltblown filaments.

7. The absorbent elastic nonwoven material of claim 1, wherein the thermoplastic elastomeric filaments comprise a polymer selected from the group consisting of styrene-isoprene-styrene block copolymers, styrene-butadiene-styrene block copolymers, styrene-ethylene/butylene-styrene block copolymers, styrene-ethylene/-propylene-styrene block copolymers, polyurethanes, elastomeric polyamides, elastomeric polyesters, elastomeric polyolefin homopolymers and copolymers, atactic polypropylenes, ethylene vinyl acetate copolymers, single-site or metallocene catalyzed polyolefins having a density less than about 0.89 grams/cc, and combinations thereof.

8. The absorbent elastic nonwoven material of claim 1, wherein the absorbent fibers comprise a material selected from the group consisting of rayon, cotton, cellulose, fiberized feathers, and combinations thereof.

9. The absorbent elastic nonwoven material of claim 1, wherein the fibers comprise pulp fibers.

10. The absorbent elastic nonwoven material of claim 1, wherein the superabsorbent material comprises superabsorbent particles.

11. A personal care absorbent article comprising an absorbent elastic nonwoven material, the absorbent elastic nonwoven material including, by weight of the absorbent elastic nonwoven material:
    about 5 to 18% of an elastic filament matrix including a plurality of thermoplastic elastomeric nonwoven filaments; and
    contained within the matrix, about 25–70% of absorbent fibers and about 25–70% of a superabsorbent material.

12. The personal care absorbent article of claim 11, wherein the thermoplastic elastomeric nonwoven filaments comprise substantially continuous filaments.

13. The personal care absorbent article of claim 11, wherein the absorbent fibers comprise pulp.

14. The personal care absorbent article of claim 11, comprising a diaper.

15. The personal care absorbent article of claim 11, comprising training pants.

16. The personal care absorbent article of claim 11, comprising swim wear.

17. The personal care absorbent article of claim 11, comprising absorbent underpants.

18. The personal care absorbent article of claim 11, comprising a baby wipe.

19. The personal care absorbent article of claim 11, comprising an adult incontinence product.

20. The personal care absorbent article of claim 11, comprising a feminine hygiene product.

21. A medical absorbent article comprising an absorbent elastic nonwoven material, the absorbent elastic nonwoven material including, by weight of the absorbent elastic nonwoven material:
    about 5 to 18% of an elastic filament matrix including a plurality of thermoplastic elastomeric nonwoven filaments; and
    contained within the matrix, about 25–70% of absorbent fibers and about 25–70% of a superabsorbent material.

22. The medical absorbent article of claim 21, wherein the thermoplastic elastomeric nonwoven filaments comprise substantially continuous filaments.

23. The medical absorbent article of claim 21, wherein the absorbent fibers comprise pulp.

24. The medical absorbent article of claim 21, comprising an underpad.

25. The medical absorbent article of claim 21, comprising a bandage.

26. The medical absorbent article of claim 21, comprising a drape.

27. The medical absorbent article of claim 21, comprising a medical wipe.

28. The absorbent elastic nonwoven material of claim 9, wherein the pulp fibers comprise short length pulp fibers.

29. The personal care absorbent article of claim 13, wherein the pulp fibers comprise short length pulp fibers.

30. The personal care absorbent article of claim 23, wherein the pulp fibers comprise short length pulp fibers.

* * * * *